(12) United States Patent
Dikovskiy et al.

(10) Patent No.: US 8,323,687 B2
(45) Date of Patent: Dec. 4, 2012

(54) PHARMACEUTICAL COMPOSITION FOR THE PREVENTION AND TREATMENT OF BONE TISSUE RESORPTION OF VARIOUS ETIOLOGY

(76) Inventors: Aleksander Vladimirovich Dikovskiy, Moscow (RU); Boris Anatolievich Rudoy, Moscow (RU); Oleg Valentinovich Dorozhko, Moscow (RU)

( * ) Notice: Subject to any disclaimer, the term of this patent is extended or adjusted under 35 U.S.C. 154(b) by 207 days.

(21) Appl. No.: 12/933,645

(22) PCT Filed: Mar. 18, 2008

(86) PCT No.: PCT/RU2008/000513
§ 371 (c)(1),
(2), (4) Date: Nov. 15, 2010

(87) PCT Pub. No.: WO2009/116888
PCT Pub. Date: Sep. 24, 2009

(65) Prior Publication Data
US 2011/0262528 A1    Oct. 27, 2011

(51) Int. Cl.
*A61K 9/127*    (2006.01)
*A01N 57/00*    (2006.01)
(52) U.S. Cl. ........................ 424/450; 514/108
(58) Field of Classification Search .................. None
See application file for complete search history.

(56) References Cited

U.S. PATENT DOCUMENTS
6,905,701 B2 * 6/2005 Pauletti et al. ............... 424/433
* cited by examiner

*Primary Examiner* — Brian Gulledge
*Assistant Examiner* — Snigdha Maewall
(74) *Attorney, Agent, or Firm* — John Alumit

(57) ABSTRACT

The invention relates to medicine and pharmacology, and represents a pharmaceutical composition for the treatment of bone resorption of various etiology comprising, as the biologically active ingredient, liposomes with biphosphonates in gel dosage form suitable for transdermal delivery of biphosphonates and effective local therapy. Using this composition, methods for the prevention and treatment of osteoporosis, Paget's disease, patological fractures associated with oncological diseases, and some other pathological processes associated with bone resorption and reparation are proposed.

4 Claims, 2 Drawing Sheets

PHARMACEUTICAL COMPOSITION FOR THE PREVENTION AND TREATMENT OF BONE TISSUE RESORPTION OF VARIOUS ETIOLOGY

CROSS-REFERENCE TO RELATED APPLICATION

This application claims the benefit of the priority filing date in PCT/RU2008/000153 and referenced in WIPO Publication WO/2009/116888. The earliest priority date claimed is Mar. 18, 2008.

FEDERALLY SPONSORED RESEARCH

None

SEQUENCE LISTING OR PROGRAM

None

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

Pertinent Art. The claimed group of inventions relates to medicine, and specifically to medicinal preparations and compositions used for the prevention and treatment of bone resorption, namely, osteoporosis, Paget's disease, and pathological fractures in cancer patients, as well as for the prevention of osteoporosis in menopause.

Prior Art. When introduced into warm-blooded organisms, sodium alendronate exhibits osteoselectivity and interacts with bone tissue as a specific inhibitor of osteoclast-mediated bone resorption. As a synthetic analogue of pyrophosphate, sodium alendronate specifically binds to hydroxyapatite of bones, thus preventing resorption of bone tissue.

At the same time, sodium alendronate as a medicinal preparation has significant shortcomings, for instance, extremely low bioavailability (under 1%) when taken orally; it often causes complications associated with irritation and mucosal ulceration of the gastrointestinal tract (GIT), and hence, cannot be prescribed for a substantial group of patients suffering from diseases of the GIT.

It is generally accepted that the entrance of biphosphonates into systemic circulation, even in the case of intravenous injection, is not a matter of principle in the treatment of osteoporosis or other diseases with bone resorption. The main thing is the delivery, distribution and exposure of biphosphonates on the surface of porous bones.

It is well known that biophosphonates can be absorbed when applied on the skin. Ferrini P. G. et al. proposed methods for optimization of penetration of salts of diphosphone acids through the skin (EP 0407344, published Feb. 27, 1991). The method's shortcoming is the fact that biophosphonates in proposed formulations have a hard time penetrating subcutaneous fat and are rapidly eliminated from the "depot." Furthermore, in order to optimize transdermal transport, additional elements are used that can cause skin irritation or allergic reactions.

Proposed is a method for the local application of sodium alendronate by the delivery of soft capsules or cream in vaginal suppositories through vaginal mucosa (U.S. Pat. No. 6,905,701, published Jun. 14, 2005). However, this method has significant shortcomings caused by the irritation effect of alendroate on mucosa and by limitations on the use of the preparation related to a patient's gender. Known from prior art is the local use of sodium alendronate for the prevention and treatment of bone desorption of various etiology, wherein the delivery of the active ingredient is done using ionophoresis (U.S. Pat. No. 6,008,206, published Dec. 28, 1999). The shortcoming of this proposal is the fact that the delivery of sodium alendronate by ionophoresis makes it possible to obtain insignificant concentrations of the preparation at the point of entry and requires the use of special medical equipment.

The closest to the proposed invention as far as the technical essence is concerned is a pharmaceutical composition for the treatment of osteoarthritis and osteoporosis of varying etiology, comprising sodium alendronate, white vaseline, salicyl alcohol, white bees wax, glycerin, liquid paraffin, sodium lourilsulphate and water, as well as a method for the local application of sodium alendronate, that includes selective delivery of the preparation to places of increased resorption of bone tissue (U.S. Pat. No. 5,958,908, published Sep. 28, 1999).

The shortcomings of this composition and method of application is the impossibility of ensuring the necessary concentration of sodium alendronate in tissues and bones directly in the area of localization of the pathological process due to the low penetrability of the active substance in the base proposed by the authors.

Disclosure of Invention. The technical result of the claimed group of inventions is that the proposed contents of the composition for transdermal delivery makes it possible to ensure a sufficiently high concentration of sodium alendronate in tissues and bones directly in the area that the preparation is applied to the skin, without using additional medical equipment or techniques (e.g., ionophoresis, electrophoresis, massage infriction, and injection of the preparation).

The objective of the proposed group of inventions, connected by a single inventive idea and related by a single inventive concept, is the creation of a pharmaceutical composition of sodium alendronate in a gel dosage form and a method for using it for transdermal application. Under the method, sodium alendronate or other biphosphonates are in liposomes which substantially improve the bioavailability of sodium alendronate and create conditions for long-term local retention of therapeutic concentrations of sodium alendronate in places of bone resorption of various etiology, in pathologic fractures, and other conditions associated with the need to repair bone tissues.

The essence of the invention, as far as the pharmaceutical composition in gel dosage form for the prevention and treatment of osteoporosis and other conditions associated with the need to repair bone tissue are concerned, is that it includes biphosphonate as an active ingredient, wherein biphosphonate is incorporated into phospholipid vesicles formed from the lipid and hydrophilic phases that include ingredients with the following ratio, mass %:

| | |
|---|---|
| biphosphonate | 0.01-2.0; |
| egg lecithin | 1.0-6.0; |
| essential pine oil | 0.05-0.2; |
| camphor oil | 0.01-1.0; |
| olive oil | 0.01-5.0; |
| vitamin E | 0.01-0.15; |
| vitamin D | 0.01-0.2; |
| carbopol | 0.4-0.6; |
| NaOH | 0.42; |
| glycerin | 2.0-4.0; |
| nipagin | 0.3; |
| nipasol | 0.1; |
| water | the rest. |

Preferably, biphosphonate is selected from the following group: alendronate, risedronate, etidronate, clodronate, and pamidronate, wherein the dimensions of phospholipid vesicles that include biphosphonate are in a range from 50 nm to 250 nm.

The essence of the invention, as far as the method for the treatment of resorption of bone tissue of various etiology is concerned, is that said pharmaceutical composition in gel dosage form includes biphosphonate as an active ingredient, wherein biphosphonate is incorporated into phospholipid vesicles formed from lipid and hydrophilic phases that include ingredients in the following ratio, mass %; biphosphonate 0.01-2.0; egg lecithin 1.0-6.0; essential pine oil 0.05-0.2; camphor oil 0.01-1.0; olive oil 0.01-5.0; vitamin E 0.01-0.15; vitamin D 0.01-0.2; carbopol 0.4-0.6; NaOH 0.42; glycerin 2.0-4.0; nipagin 0.3; nipasol 0.1; water the rest. Preferably, biphosphonate is selected from the following group: alendronate, risedronate, etidronate, clodronate, pamidronate, wherein the dimensions of the phospholipid vesicles that include biphosphonate are in a range from 50 nm to 250 nm. The gel is applied on the skin at places of diagnosed resorption or destruction of bone tissue.

The essence of the invention, as far as the method for the treatment of osteoporosises in patients with pathology of the gastrointestinal tract organs is concerned, is that said pharmaceutical composition in gel dosage form includes, as an active ingredient, biphosphonate incorporated in phospholipid vesicles formed from lipid and hydrophilic phases that include ingredients with the following ratio, mass %: biphosphonate 0.01-2.0; egg lecithin 1.0-6.0; essential pine oil 0.05-0.2; camphor oil 0.01-1,0; olive oil 0.01-5.0; vitamin E 0.01-0.15; vitamin D 0.01-0.2; Carbopol 0.4-0.6; NaOH 0.42; glycerin 2.0-4.0; Nipagin 0.3; Nipasol 0.1; water the rest. Preferably, biphosphonate is selected from the following group: alendronate, risedronate, etidronate, clodronate, pamidronate, wherein the dimensions of the phospholipid vesicles that include biphosphonate are in a range from 50 nm to 250 nm. Transdermal application of gel in this case excludes GIT blennosis that is typical when taking biphosphonates orally.

DRAWINGS

DETAILED DESCRIPTION

Figure 1:
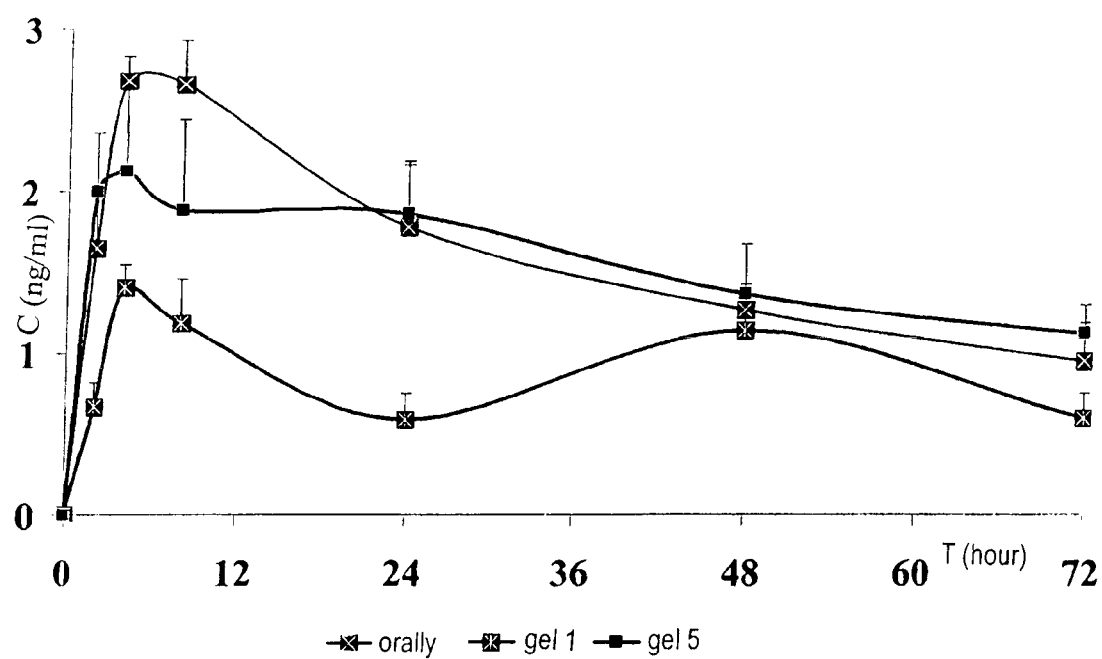
FIG. 1 shows kinetic curves of concentrations of sodium alendronate in the plasma of experimental white rats after oral administration, and after a single and five-time application in liposomal gel on the inner thigh skin.

The above result is achieved due to the fact that in the claimed pharmaceutical composition for the prevention and treatment of bone resorption of various etiology that comprises an active ingredient—sodium alendronate, the latter is incorporated in phospholipid vesicles formed from lipid and hydrophilic phases, wherein the lipid phase includes egg lecithin, essential oil of pine, camphor and olive oils, vitamins E, D and F, and the hydrophilic phase includes sodium alendronate. The composition additionally comprises a gelling agent that includes carbopol, NaOH 10% , a plasticizer—glycerin, preservatives—nipagin, nipasol, and water in the following ratio of ingredients by composition, mass %:

| | |
|---|---|
| sodium alendronate | 0.01-0.1 |
| egg lecithin | 1-6 |
| essential pine oil | 0.05-0.2 |
| camphor oil | 0.01-1 |
| olive oil | 0.01-5 |
| vitamin E | 0.01-0.15 |
| vitamin D | 0.01-0.2 |
| vitamin F | 0.2-0.4 |
| carbopol | 0.4-0.6 |
| NaOH | 0.42 |
| glycerin | 2-4 |
| nipagin | 0.3 |
| nipasol | 0.1 |
| water | the rest, | wherein the ingredients are treated in a high-speed homogenizer in which monolayer liposomes with certain dimensions—which are produced as a result of treatment of fat-soluble ingredients—are formed. The result is also achieved because the pharmaceutical composition containing liposomes, with sodium alendronate in gel form, is applied on the skin directly in places of diagnosed resorption of bone tissue (points of fractures, joints, vertebrae, etc.).

Active transport of medicinal and biologically active substances in liposomes has been proven numerous times (for instance, patent RF No. 2167650, BI [Bulletin of Inventions] No. 15, 2001). By enclosing them in liposomes, it was not only possible to deliver medicinal substances to organs—targets, but in a number of cases it was also possible to significantly reduce their required concentration, which is very important in cases of medicinal agents that have side effects.

The objective of the proposed invention is to produce liposomal pharmaceutical compositions of biphosphonates for transdermal transport comprising alendronate, risedronate, etidronate, clodronate, pamidronate and other ingfredients as active ingredients, and that are supposed to be used in conditions associated with resorption of bone tissue as the result of osteoporosis and bone regeneration in cases of pathologic fractures, osteoplastic, osteoplasty, etc.

The contents of the proposed pharmaceutical composition, which comprises a gelling agent, a plasticizer, a lipid phase, a hydrophilic phase, biphosphonates, a preservative, essential oil and water, is represented using the following examples:

EXAMPLE 4

| | |
|---|---|
| sodium alendronate | 0.01 |
| egg lecithin | 2.0 |
| essential pine oil | 0.05 |
| camphor oil | 0.05 |

-continued

| | |
|---|---|
| olive oil | 1.0 |
| vitamin E | 0.1 |
| vitamin D | 0.1 |
| vitamin F | 0.2 |
| carbopol | 0.4 |
| NaOH | 0.42 |
| glycerin | 2.0 |
| nipagin | 0.3 |
| nipasol | 0.1 |
| water | the rest |

EXAMPLE 5

| | |
|---|---|
| sodium alendronate | 0.05 |
| carbopol | 0.5 |
| glycerin | 4.0 |
| NaOH | 0.42 |
| egg lecithin | 1.0 |
| vitamin E | 0.05 |
| vitamin D | 0.1 |
| vitamin F | 0.2 |
| camphor oil | 0.4 |
| olive oil | 2.0 |
| essential pine oil | 0.1 |
| nipagin | 0.3 |
| nipasol | 0.1 |
| water | the rest |

EXAMPLE 6

| | |
|---|---|
| sodium alendronate | 0.1 |
| carbopol | 0.6 |
| glycerin | 4.0 |
| NaOH | 0.42 |
| egg lecithin | 3.0 |
| оЛИвковое масЛо | 5.0 |
| vitamin E | 0.15 |
| vitamin D | 0.1 |
| vitamin F | 0.2 |
| essential pine oil | 0.2 |
| nipagin | 0.3 |
| nipasol | 0.1 |
| water | the rest |

The pharmaceutical composition—with sodium alendronate included in very small (from 50 nm to 200 nm) vesicular particles and stabilized in a system of polymers varying in nature that acts as an inhibitor of osteo-mediated bone resorption—can be used for the correction of bone resorption in cases of osteoporosis in women in the post-menopause period. The use of the proposed composition substantially reduces the number of compression fractures of the spine and femoral neck and reduces bone porosity in old age, both in women and men. The liposomal composition with biphosphonates which is used in gel form ensures high bioavailability and active transport of the composition in deep layers of hypoderm, muscle and connective tissue, and surrounding bones.

Transdermal delivery of the composition is accomplished easily by applying it to the skin in a specific amount of gel containing a stable suspension of liposomes in the projection of diagnosed bone porosity or in places of reparation of bone tissue as the result of fractures. The use of liposomes makes it possible to optimize the concentration of active substances in gel, which makes it possible to achieve a maximum therapeutic effect, and also to perform the transport of biphosphonates to an area of specific spine sections, tubular bones, joints and tissues surrounding porous or deformed bones.

The proposed liposomal composition makes it possible to effectively use properties of sodium alendronate or other biphosphonates, use additional active substances, and also eliminate the deficiency of phospholipids in places of gel application. The method of delivery of sodium alendronate to places of bone resorption consists of applying a specific amount of liposomal gel with biphosphonates on the skin in the projection of defects of bone tissue, compression fractures of the spine and femoral neck, or in places of resorption of bone tissue in cases of fracture therapy or osteoplasty. The composition is produced as follows. First, the pharmaceutical composition ingredients are dispersed according to the above formulation. The resulting mixture of liposomes with incorporated sodium alendronate is stabilized using a gelling agent. Then, glycerin, a plasticizer, and preservatives are added. The manufacturing process of gel preparation comprise the following stages.

1. Ingredient Preparation.
   1.1. Polymer dissolution.
   1.2. Producing a glycerin-preservative mixture.
   1.3. Mixing additional ingredients—egg lecithin, olive oil, castor oil, essential oil of pine, vitamins E, D, F.
2. Mixing the hydrophilic and hydrophobic phases. Mixing is performed in a homogenizer in high-speed mode at room temperature. The active ingredient is added to the ready suspension of lipid vesicles obtained by neutralization. Homogenization is performed at the blender maximum rpm for 5-10 min. Then, a preserving complex is added, and the mass is mixed at a control pH=6.9-7.4.

The entire process can be conducted using a PGR-2 unit with a generator of hydroacoustic oscillations. Alternatively, if there is an efficient blender-homogenizer that produces liposomes, one can use the method of ultrasound treatment or the method of extrusion through membrane filters.

Liposome dimensions and the number of plies are controlled using electronic microscopy or spectrophotometry.

Clinical and Experimental Studies. The effectiveness and safety of the gel form of biphosphonates was tested in clinical studies on volunteers. The pharmaceutical composition was tested on 62 volunteers, both women and men, of various ages—from 32 to 75 years old, with various condition and bone tissue density. The duration of clinical observations of patients was at least six months. The clinical status of the experimental group was evaluated with an observational frequency of once a month compared to the control group (the known means of and methods for prevention and treatment of bone resorption).

During the first stage, before clinical testing, all patients were given cutaneous allergy tests with the experimental gel. No cases of skin irritation symptoms or local or general allergic reactions were observed.

The professionals who conducted the tests, as well as tests subjects themselves, noted that the agent was convenient in practical application, including during massage.

EXAMPLE 7

Patient B., female, 53 years old, osteoporosis with underlying immunopathy, aching pain in tubular bones. Application of the gel with sodium alendronate considerably alleviated patient's condition after 1.5 months of treatment: joint mobility increased, swelling and pain decreased, as did morning stiffness.

EXAMPLE 8

Patient G., male, 66 years old, diagnosis: gonarthrosis on the right. Application of gel with sodium alendronate for three months considerably improved patient's condition: abatement of pain syndrome was recorded, and the range of knee joint motion increased significantly. Increased bone tissue density and reduction of events of osteoporosis were confirmed by densitometry.

EXAMPLE 9

Patient A., female, 55 years old, diagnosis: postmenopausal osteoporosis. To alleviate patient's condition, the gel with sodium alendronate was prescribed; skin applications were administered to the patient daily for three months. During follow-up examination of the patient after three months, positive changes were noted in the densitogram, as well as increased knee and hip joint motion and higher tolerance to loads.

Figure 2:
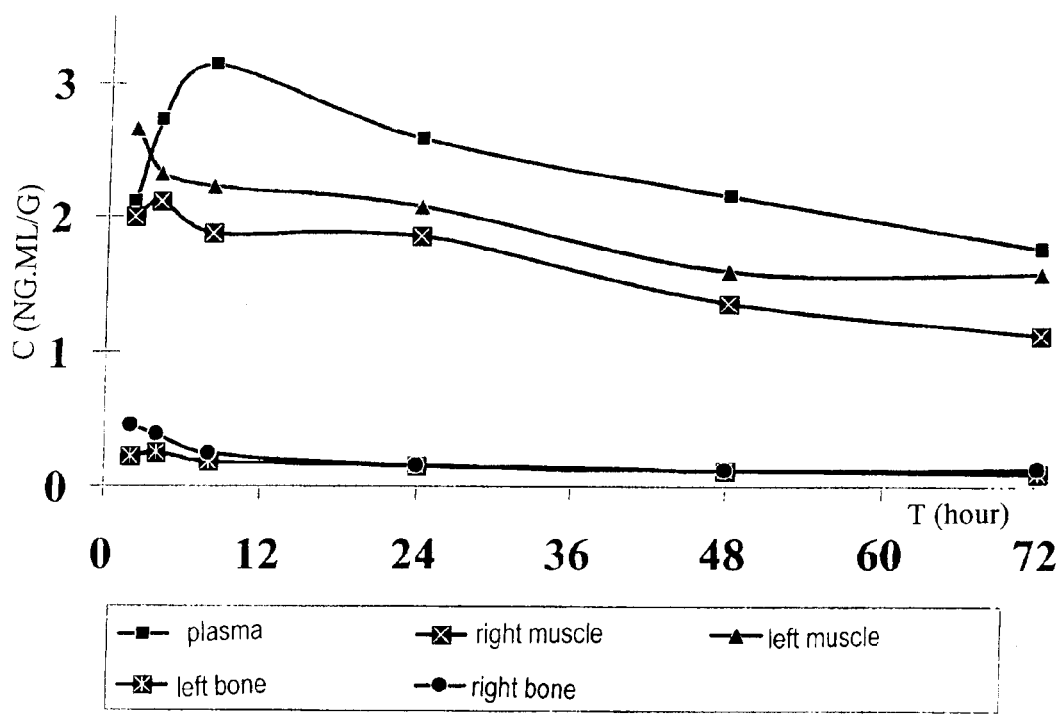
FIG. 2 shows kinetic curves of concentrations of sodium alendronate in the plasma of blood of white rats in thigh muscular tissue and in femoral bones after a five-time skin application of sodium alendronate in liposomal gel form on the inner thigh surface of rats in the 1 mg (4.80±0.34 mg/kg) dose.

Experimental studies of pharmaceutical kinetics of the liposomal pharmaceutical composition with sodium alendronate in vivo were conducted based at GU [State Institution] V.V. Zakusov Nil [Scientific Research Institute] of Pharmacology, RAMN [Russian Academy of Medical Sciences] using the radionuclide method on 152 outbred white rats with 180-220 g mass. Tritium-labeled sodium alendronate with specific radioactivity of 30 µCi/mg, in a 1 mg dose, was used for oral administration and skin application in the form of gel wherein sodium alendronate with a radioactive label was in liposomes. In the experiments, the results of which are shown in FIGS. 1 and 2, the content of the labeled products was determined in the plasma and muscular and bone tissues of rats, and in urine and feces. The specimens were analyzed 2, 4, 8, 12, 24, 48 and 72 hours after oral administration of the preparation and skin application of the gel on the epilated inner hip of laboratory animals. As a result of the experiments, the results of which are shown in FIGS. 1 and 2, the following was found:

- the proposed composition is a "long-lived" one and lasts in rat organisms for 72 hours;
- relative bioavailability of sodium alendronate in gel after a five-time application on rat skin is 2.63 times higher than in the case of a single application and 1.46 times higher than in the case oral administration of the preparation.
- skin application of sodium alendronate in gel dosage form results in doubling of the preparation's half-elimination period compared to oral administration.

As a result, the composition's content and methods for transdermal delivery make it possible to provide a sufficiently high concentration of sodium alendronate in tissues and bones directly in the area of in which the preparation is applied to the skin, without additional medical equipment or techniques (ionophoresis, electrophoresis, massage infriction, injection of the preparation).

In doing this, a pharmaceutical composition of sodium alendronate in gel dosage form has been created, as well as a method for transdermal application thereof, wherein sodium alendronate or other biphosphonates are part of liposomes that considerably improve the bioavailability of sodium alendronate and create conditions for a long-lasting local retention of therapeutic concentrations of sodium alendronate in places of bone resorption of various etiology, in cases of pathological fractures and other conditions associated with the need to repair bone tissue.

Industrial Applicability. The invention is realized using universal equipment widely used in industrial production of soft medicinal forms.

The invention claimed is:

1. A pharmaceutical composition in gel dosage form for the treatment of osteoporosis, that includes biphosphonate as an active component, wherein the biphosphonate is incorporated in phospholipid vesicles formed from lipid and hydrophilic phases comprising ingredients with the following amounts, based on mass %:

| | |
|---|---|
| biphosphonate | 0.01-2.0; |
| egg lecithin | 1.0-6.0; |
| essential pine oil | 0.05-0.2; |
| camphor oil | 0.01-1.0; |
| olive oil | 0.01-5.0; |
| vitamin E | 0.01-0.15; |
| vitamin D | 0.01-0.2; |
| carbopol | 0.4-0.6; |
| NaOH | 0.42; |
| glycerin | 2.0-4.0; |
| nipagin | 0.3; |
| nipasol | 0.1; and |
| the rest, water. | |

2. The pharmaceutical composition in gel dosage form of claim 1, wherein the biphosphonate is selected from the following group: alendronate, risedronate, etidronate, clodronate, and pamidronate.

3. The parmaceutical composition in gel dosage form of claim 1, wherein the dimensions of the phospholipid vesicles comprising biphosphonate are in the range of 50 nm to 250 nm.

4. A method for the treatment of osteoporosis wherein the biphosphonates in the liposomal gel of claim 1 are applied transdermally, which eliminates the development of complications associated with gastrointestinal tract blennosis when biphosphonates are taken orally.

* * * * *